(12) United States Patent
Yelvington

(10) Patent No.: US 9,446,279 B1
(45) Date of Patent: Sep. 20, 2016

(54) RESISTANCE-APPLYING GARMENT AND CONNECTORS USED IN FORMING GARMENT

(71) Applicant: Christopher Joseph Yelvington, Saint Johns, FL (US)

(72) Inventor: Christopher Joseph Yelvington, Saint Johns, FL (US)

( * ) Notice: Subject to any disclaimer, the term of this patent is extended or adjusted under 35 U.S.C. 154(b) by 25 days.

(21) Appl. No.: 14/459,619

(22) Filed: Aug. 14, 2014

Related U.S. Application Data

(63) Continuation-in-part of application No. 13/947,175, filed on Jul. 22, 2013.

(51) Int. Cl.
*A63B 21/02* (2006.01)
*A63B 21/055* (2006.01)

(52) U.S. Cl.
CPC ................ *A63B 21/0552* (2013.01)

(58) Field of Classification Search
CPC .......... A63B 21/1449; A63B 21/0552; A63B 21/0557; A63B 21/0555; A63B 21/02; A63B 21/065; A63B 21/1484; A63B 23/03508; A63B 21/16; A63B 21/026; A41D 13/08; A41D 20/00; A41D 19/01588; A41D 19/0044; A41D 19/0048; A41D 19/015; A41D 19/01582; A41D 27/10; A41D 19/01511; A41D 13/0518; A41D 19/0006; A41D 19/0062; A41D 2500/30; A41D 13/088; A41D 2400/52; A41D 17/00; A61H 1/008; A61H 2201/1635; A61H 2201/165; A61H 2205/06; A61H 3/02; A61H 1/0218; A61H 1/0277; A61H 1/0281; A61H 2003/025; A61H 2201/0107; A61H 2201/1481; A61H 2201/149; A61H 2201/1614; A61H 2201/1621; A61H 2201/1638; A61H 2201/164; A61H 2201/1642; A61H 2201/1664; A61H 2205/104; A61H 3/0277; A61H 13/10; A61H 13/107; A41F 9/025; A41F 11/16
USPC ....... 482/121, 124; 2/69, 227, 16, 20, 161.6, 2/162, 170, 61, 242; 128/846, 849, 856, 128/869–882; 602/6–8, 20–23, 30, 62, 64; D8/356

See application file for complete search history.

(56) References Cited

U.S. PATENT DOCUMENTS

| 101,743 A * | 4/1870 | King ....................... A61F 13/04 24/484 |
| 1,706,992 A * | 3/1929 | Ayer ........................ B60M 5/00 403/281 |
| 2,117,974 A * | 5/1938 | Moore .................... D03D 15/08 139/388 |
| 2,956,108 A * | 10/1960 | Brenner ................. H01R 4/186 174/71 R |
| 3,053,930 A * | 9/1962 | Mallanik ................ H01R 4/186 174/71 R |
| 3,235,654 A * | 2/1966 | Eldridge, Jr. .......... H01R 4/186 174/71 R |

(Continued)

*Primary Examiner* — Loan H Thanh
*Assistant Examiner* — Andrew S Lo
(74) *Attorney, Agent, or Firm* — Glenn E. Gold, P.A.

(57) ABSTRACT

A resistance-applying garment includes an elastic line arranged in a zigzag pattern and a plurality of connectors connecting side-by-side pairs of portions of the line so as to form an assembled tubular mesh netting structure having an endless sidewall and open opposite ends in which none of the portions of the line cross over one another and the connectors are disposed about the exterior of the endless sidewall. Each connector has a body with a pair of passageways defined therethrough between opposite outer end portions and an inner middle portion of the body and extending between front and rear faces thereof and spaced from top and opposite outer sides thereof. Line portions are received and removably retained in the passageways. Top side and opposite outer sides of the body define a U-shaped outer surface arcuate-shaped and extending to and between the front and rear faces.

11 Claims, 11 Drawing Sheets

(56) References Cited

U.S. PATENT DOCUMENTS

| | | | | |
|---|---|---|---|---|
| 3,290,746 A * | 12/1966 | Broske | H01R 4/50 | |
| | | | 174/71 R | |
| 3,307,546 A * | 3/1967 | Cherio | A61F 13/00038 | |
| | | | 602/60 | |
| 3,322,888 A * | 5/1967 | Zemels | H01R 4/186 | |
| | | | 174/71 R | |
| 3,329,928 A * | 7/1967 | Broske | H01R 4/08 | |
| | | | 174/94 R | |
| 3,419,003 A * | 12/1968 | Krauss | A61F 13/00021 | |
| | | | 450/93 | |
| 3,487,161 A * | 12/1969 | James | B21F 15/08 | |
| | | | 174/84 R | |
| 3,636,595 A * | 1/1972 | Wines | A01G 25/00 | |
| | | | 24/339 | |
| 4,002,349 A * | 1/1977 | Dopp | A63C 11/021 | |
| | | | 280/809 | |
| 4,047,400 A * | 9/1977 | Thorneburg | A41D 20/00 | |
| | | | 2/170 | |
| 4,294,240 A * | 10/1981 | Thill | A61F 13/041 | |
| | | | 602/21 | |
| 4,308,872 A * | 1/1982 | Watson | A61B 5/1135 | |
| | | | 600/534 | |
| 4,378,009 A * | 3/1983 | Rowley | A61F 5/012 | |
| | | | 128/DIG. 20 | |
| 4,456,015 A * | 6/1984 | Sackner | A61B 5/1073 | |
| | | | 600/534 | |
| 4,688,961 A * | 8/1987 | Shioda | F16B 7/04 | |
| | | | 24/336 | |
| 4,750,339 A * | 6/1988 | Simpson, Jr. | D02G 3/32 | |
| | | | 2/162 | |
| 4,768,502 A * | 9/1988 | Lee | A61F 5/05866 | |
| | | | 602/20 | |
| 4,854,310 A * | 8/1989 | Lee | A61F 5/05866 | |
| | | | 602/21 | |
| D345,252 S * | 3/1994 | Randall | D2/901 | |
| 5,331,725 A * | 7/1994 | Chou | E04H 17/18 | |
| | | | 24/339 | |
| 5,599,288 A * | 2/1997 | Shirley | A61F 5/0123 | |
| | | | 602/16 | |
| 5,672,150 A * | 9/1997 | Cox | A61F 5/0118 | |
| | | | 128/879 | |
| D390,066 S * | 2/1998 | Watkins | D7/633 | |
| 5,720,042 A * | 2/1998 | Wilkinson | A41D 13/0015 | |
| | | | 2/69 | |
| 5,836,902 A * | 11/1998 | Gray | A61F 5/0111 | |
| | | | 128/882 | |
| 5,857,947 A * | 1/1999 | Dicker | A63B 21/4025 | |
| | | | 2/69.5 | |
| 5,873,130 A * | 2/1999 | Lafferty | A41D 13/088 | |
| | | | 2/159 | |
| D406,749 S * | 3/1999 | Selk | D8/356 | |
| 5,931,798 A * | 8/1999 | Green | A61F 13/04 | |
| | | | 602/6 | |
| D421,715 S * | 3/2000 | Won | D8/395 | |
| 6,048,253 A * | 4/2000 | Larsen | A41C 1/10 | |
| | | | 2/44 | |
| 6,053,852 A * | 4/2000 | Wilkinson | A41D 13/0015 | |
| | | | 2/69 | |
| 6,231,488 B1 * | 5/2001 | Dicker | A41D 13/0015 | |
| | | | 2/69 | |
| 6,308,332 B1 * | 10/2001 | Tollini | A44B 18/00 | |
| | | | 119/856 | |
| 6,425,876 B1 * | 7/2002 | Frangi | A61F 5/0109 | |
| | | | 128/882 | |
| 6,461,307 B1 * | 10/2002 | Kristbjarnarson | A61B 5/1135 | |
| | | | 600/529 | |
| 6,613,006 B1 * | 9/2003 | Asherman | A61F 13/04 | |
| | | | 602/20 | |
| 6,629,598 B2 * | 10/2003 | Narula | A61F 5/05841 | |
| | | | 206/5 | |
| 6,665,876 B1 * | 12/2003 | Newman | A41D 13/08 | |
| | | | 2/207 | |
| 6,813,779 B1 * | 11/2004 | Williams | A41D 13/08 | |
| | | | 2/16 | |
| 6,942,628 B1 * | 9/2005 | Watson | A61F 13/04 | |
| | | | 602/6 | |
| 7,195,434 B1 * | 3/2007 | Kuo | B60R 7/005 | |
| | | | 410/118 | |
| 7,316,175 B2 * | 1/2008 | Safwat | A01K 75/00 | |
| | | | 87/53 | |
| D581,255 S * | 11/2008 | Calvin | D8/356 | |
| 7,615,022 B2 * | 11/2009 | Nordt, III | A61F 5/0106 | |
| | | | 602/16 | |
| D618,985 S * | 7/2010 | Sjoqvist | D8/356 | |
| 7,762,970 B2 * | 7/2010 | Henderson | A61F 5/05866 | |
| | | | 128/878 | |
| 7,934,395 B2 * | 5/2011 | Zhu | A41D 19/01511 | |
| | | | 2/16 | |
| 8,388,616 B2 * | 3/2013 | Vogel | A61F 2/2475 | |
| | | | 606/157 | |
| 8,486,507 B2 * | 7/2013 | De Luca | B29C 44/5654 | |
| | | | 428/131 | |
| D696,576 S * | 12/2013 | Ng | D8/394 | |
| 8,733,293 B2 * | 5/2014 | Link | A01K 1/0017 | |
| | | | 119/474 | |
| D720,606 S * | 1/2015 | Mathews | D8/356 | |
| 8,986,234 B2 * | 3/2015 | Summit | | |
| D727,717 S * | 4/2015 | Byrne | D8/356 | |
| D733,535 S * | 7/2015 | Egami | D8/356 | |
| 2002/0052568 A1 * | 5/2002 | Houser | A42B 3/00 | |
| | | | 602/26 | |
| 2006/0026733 A1 * | 2/2006 | Nordt, III | A41D 13/05 | |
| | | | 2/69 | |
| 2006/0026736 A1 * | 2/2006 | Nordt, III | A41D 13/05 | |
| | | | 2/125 | |
| 2006/0030804 A1 * | 2/2006 | Nordt, III | A41D 13/05 | |
| | | | 602/26 | |
| 2006/0030805 A1 * | 2/2006 | Nordt, III | A41D 13/05 | |
| | | | 602/26 | |
| 2006/0185059 A1 * | 8/2006 | Taha | A41D 19/0089 | |
| | | | 2/170 | |
| 2008/0154164 A1 * | 6/2008 | Sheehan | A61F 5/01 | |
| | | | 602/7 | |
| 2008/0295216 A1 * | 12/2008 | Nordstrom | A41D 13/0015 | |
| | | | 2/69 | |
| 2010/0036300 A1 * | 2/2010 | Sheehan | A61F 5/05825 | |
| | | | 602/7 | |
| 2010/0056973 A1 * | 3/2010 | Farrow | A61F 13/08 | |
| | | | 602/63 | |
| 2010/0144490 A1 * | 6/2010 | Purdy | A63B 21/0004 | |
| | | | 482/1 | |
| 2010/0205710 A1 * | 8/2010 | Aloy Font | A41D 1/08 | |
| | | | 2/22 | |
| 2011/0066093 A1 * | 3/2011 | Vess | A61H 11/00 | |
| | | | 601/148 | |
| 2011/0302687 A1 * | 12/2011 | Whaley | A63B 21/0602 | |
| | | | 2/69 | |
| 2012/0174278 A1 * | 7/2012 | Spivak | A41D 13/08 | |
| | | | 2/16 | |
| 2013/0019374 A1 * | 1/2013 | Schwartz | A61F 5/00 | |
| 2013/0130874 A1 * | 5/2013 | Richardson | A63B 21/0555 | |
| | | | 482/124 | |
| 2013/0167282 A1 * | 7/2013 | Ramirez | A63B 71/14 | |
| | | | 2/21 | |
| 2013/0283511 A1 * | 10/2013 | Diamond | A63B 71/12 | |
| | | | 2/455 | |
| 2014/0109286 A1 * | 4/2014 | Blakely | A41D 31/02 | |
| | | | 2/69 | |
| 2014/0208484 A1 * | 7/2014 | Huff | A41F 9/02 | |
| | | | 2/243.1 | |
| 2014/0276308 A1 * | 9/2014 | DiAngelo | A61F 5/02 | |
| | | | 602/19 | |
| 2014/0336020 A1 * | 11/2014 | von Hoffmann | A63B 1/00156 | |
| | | | 482/124 | |
| 2014/0366245 A1 * | 12/2014 | Smalls | A42B 1/008 | |
| | | | 2/171.2 | |
| 2015/0190669 A1 * | 7/2015 | Matsuura | A63B 21/02 | |
| | | | 482/8 | |
| 2015/0309563 A1 * | 10/2015 | Connor | G06F 3/011 | |
| | | | 73/865.4 | |

* cited by examiner

RESISTANCE-APPLYING GARMENT AND CONNECTORS USED IN FORMING GARMENT

CROSS REFERENCE(S) TO RELATED APPLICATIONS(S)

This patent application is a continuation-in-part of pending U.S. patent application Ser. No. 13/947,175, filed Jul. 22, 2013, which is hereby incorporated in its entirety herein by reference thereto.

FIELD OF THE INVENTION

The present disclosure relates to improvement of athletic performance through improved application of increased resistance to muscular action and, more particularly, is related to a resistance-applying garment and connectors used in forming the garment to productively fit an arm, a leg and/or a torso of a user's body.

BACKGROUND OF THE INVENTION

Pursuit of improved athletic performance often involves the precise application of increased resistance to muscular action of selected parts of a user's body. Various garments have been devised heretofore that utilize elastic or resilient elements to provide resistance to an activity that requires swinging or bending of limbs and/or torso of the user's body. Typically, such elastic elements are elastic cords, bands or straps that are separate from the remainder of the garment or are integral with the garment.

Garments utilizing these elastic elements separate from the remainder of the garment only offer generalized external resistance that ordinarily will interfere with rather than enhance precise athletic performance. Garments utilizing these elastic elements integral with the garment have incorporated them in intertwined weaves that are complex to manufacture and assemble and create pressure points on muscles that with time and repeated motion will create discomfort and have deleterious effects.

Accordingly, there remains a need in the art for a garment construction that will overcome these deficiencies of the known art and the problems that remain unsolved.

SUMMARY OF THE INVENTION

The present invention overcomes the deficiencies of the known art and the problems that remain unsolved by providing a resistance-applying garment and connectors used in forming the garment to tailor the garment to productively fit the arms, legs and/or torso of a user's body so as to increase resistance of any athletic or work-out activity in multiple simultaneously acting planes. The garment is constructed to add resistance through the arms, legs and/or torso without preferentially over- or under-using any muscle or group, which could disrupt the timing of resistance to the body part. The garment actually permits tailoring simultaneously in three ways: weight, air resistance and elastic resistance. The resistance-applying garment of the present invention thereby enables the successful pursuit of improved athletic performance through the precise application of increased resistance uniformly to muscular action of selected parts of the user's body.

In one aspect of the present invention, a resistance-applying garment includes:
a line of elastic material arranged in a zigzag pattern; and
a plurality of connectors connecting side-by-side pairs of portions of the line of elastic material so as to form an assembled tubular mesh netting structure having an endless sidewall and open opposite ends in which none of the portions of the line of elastic material cross over one another and the connectors are disposed about the exterior of the endless sidewall;
wherein each of the connectors includes
a connector body having opposite top and bottom sides, opposite outer sides, front and rear faces, a pair of opposite outer end portions, and an inner middle portion disposed between and spaced from the outer end portions, the inner middle portion and the outer end portions also disposed between the top and bottom sides, the opposite outer sides, and the front and rear faces; and
a pair of arcuate surfaces defined between the opposite outer end portions and the inner middle portion, the pair of arcuate surfaces defining a pair of passageways extending through the connector body between the front and rear faces thereof and spaced from the top side and the opposite outer sides and having respective openings at the bottom side of the connector body through which portions of the elastic line are received and removably retained in the passageways;
wherein the top side and the opposite outer sides of the connector body define a U-shaped outer surface being arcuate-shaped and extending to and between the front and rear faces.

In another aspect of the present invention, a resistance-applying garment includes:
a tubular body having a circumference and a height extending in a transverse relationship to the circumference, the tubular body being formed by:
at least one line of elastic material arranged in a zigzag pattern so as to define a succession of elongated line portions and a succession of looped line portions between the elongated line portions such that the elongated line portions are oriented side-by-side to one another extending along the height of the tubular body and the looped line portions are oriented side-by-side to one another in two opposing rows spaced apart by the elongated line portions and extending about the circumference of the tubular body such that the looped line portions in one of the rows are in staggered relationship to the looped line portions in the other of the rows; and
a plurality of connectors connecting side-by-side pairs of the elongated line portions at multiple spaced locations thereon along the height of the tubular body so as to orient each of the elongated line portions in a sinuous pattern such that the looped line portions, and the pairs of elongated line portions connected by the connectors, provide the tubular body in the form of an assembled tubular mesh netting structure having an endless sidewall and open opposite ends in which none of the elongated line portions cross over one another, none of the looped line portions cross over one another and the connectors are disposed about the exterior of the endless sidewall;
wherein each of the connectors includes
a connector body having opposite top and bottom sides, opposite outer sides, front and rear faces, a pair of opposite outer end portions, and an inner middle portion disposed between and spaced from the outer end portions, the inner middle portion and the outer end portions also disposed between the top and bottom sides, the opposite outer sides and the front and rear faces, and a pair of arcuate surfaces defined between the opposite outer end portions and the inner middle portion, the pair of arcuate surfaces defining a pair of passageways extending through the connector body between the front and rear faces thereof and spaced from the top side and the opposite outer sides and having respective openings at the bottom side of the connector body through which each of a pair of the elongated line portions of the elastic line is received and removably retained in the passageways, wherein the top side and the opposite outer sides of the connector body define a U-shaped outer surface being arcuate-shaped and extending to and between the front and rear faces.

In yet another aspect of the present invention, a connector for connecting a pair of elongated portions of an elastic line arranged in a zigzag pattern in a garment includes:

a connector body having top and bottom sides, opposite outer sides, front and rear faces, a pair of opposite outer end portions, and an inner middle portion disposed between and spaced from the outer end portions, the inner middle portion and outer end portions also disposed between the top and bottom sides, the opposite outer sides, and the front and rear faces; and a pair of arcuate surfaces defined between the opposite outer end portions and the inner middle portion, the pair of arcuate surfaces defining a pair of passageways extending through the connector body between the front and rear faces thereof and spaced from the top side and having respective openings at the bottom side of the connector body through which each of a pair of elongated portions of an elastic line can be received and removably retained in the passageways;

wherein the top side and the opposite outer sides of the connector body define a U-shaped outer surface being arcuate-shaped and extending between and to the front and rear faces.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "top", "bottom", "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
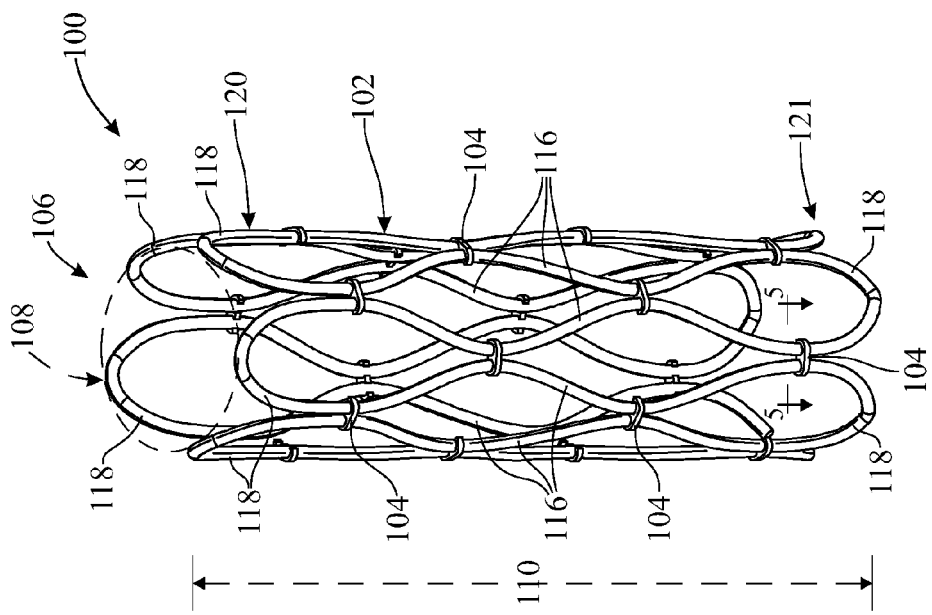
FIG. 1 presents a front isometric view of an exemplary embodiment of a resistance-applying garment in the form of an assembled tubular mesh netting structure having an endless sidewall and open opposite ends.

An exemplary embodiment of a resistance-applying garment 100 is illustrated in FIG. 1. At least one line 102 of elastic material (hereinafter termed "elastic line") and a plurality of connectors 104 are employed in forming the garment 100, as shown in FIGS. 1-4. The garment 100, the elastic line 102, and the connector 104 constitute aspects of the present invention.

Figure 2:
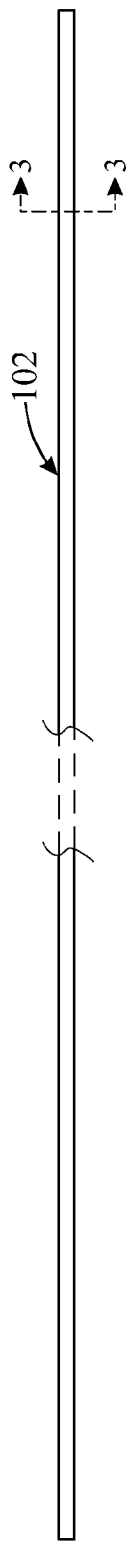
FIG. 2 presents a foreshortened side elevation view of an exemplary embodiment of a line of elastic material that can be employed to form the garment originally introduced in FIG. 1.
Figure 3:
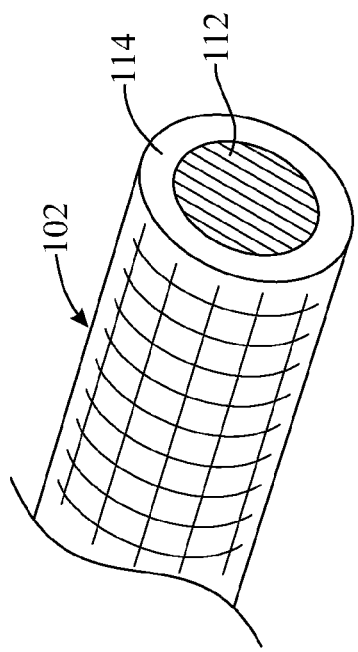
FIG. 3 presents an enlarged isometric view of a fragmentary portion of the line of elastic material of FIG. 2, showing a cross-section thereof taken along section line 3-3 of FIG. 2.
Figure 13:
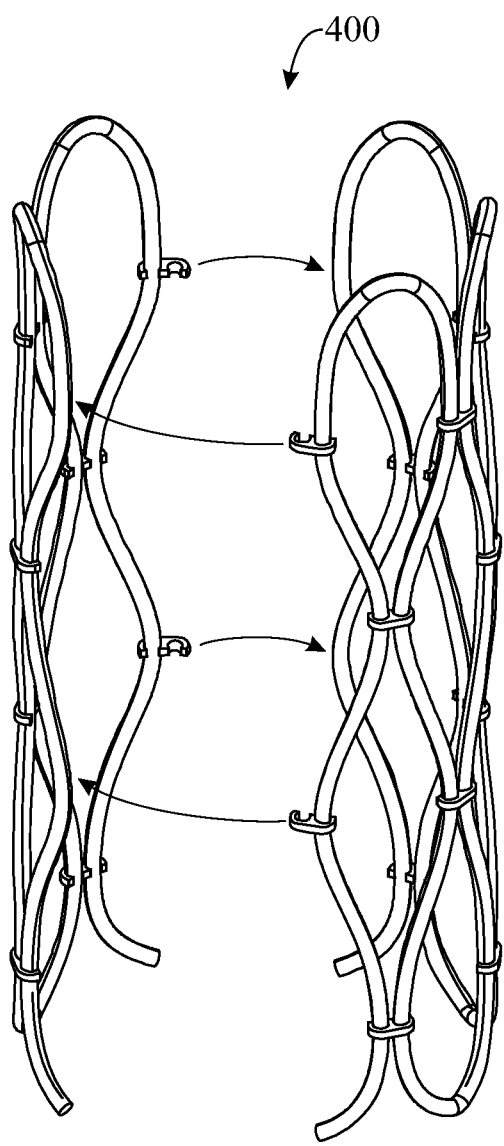
FIG. 13 presents an isometric view of another exemplary embodiment of a resistance-applying garment constructed from two of the partially assembled structure shown in FIG. 8.

In this particular implementation, the garment 100 utilizes only one elastic line 102 in an overall arrangement of a tubular body 106 having a circumference 108 and a height 110 extending in a transverse relationship to the circumference 108, as illustrated in FIG. 1. It should be noted that an alternative implementation is presented herein below (with reference to FIG. 13), incorporating a pair of mesh structures that can be selectively clipped or otherwise attached together to form a unitary configuration. Referring back to the present configuration, the single elastic line 102 of a given length end to end (being not connected to one another) is shown in FIG. 2 prior to being formed into the pattern it assumes in the tubular body 106. The term "line of elastic material" or "elastic line" is used herein in a generic sense to encompass other more specific terms, such as an elastic string, cord, rope, cable, band, etc. The elastic line 102 may have a substantially rounded configuration in cross-section, such as a circular or oval-shaped cross-sectional configuration, as seen in FIG. 3. The construction of the elastic line 102 may include an inner elastic core 112 and an outer protective casing or sheath 114, such as an inner rubber band and an outer casing as in the case of an ordinary bungee cord or rope. The outer casing may be made of any suitable material, such as nylon, cotton, rayon, polypropaline, and polyster, by way of example but not of limitation. The outer sheath 114 may have a woven tubular construction which accommodates stretching or elongating of the inner core 112. The thickness and elastic modulus of the elastic line 102 will vary depending upon the elasticity of the garment 100 that is desired. By way of example but not of limitation, the selected thickness of the elastic line 102 may range from about 6 mm to 14 mm.

The elastic line 102 in the tubular body 106 is arranged in a serpentine or zigzag pattern, as illustrated in FIG. 1. In such pattern, the elastic line 102 defines a succession of elongated line portions 116 and a succession of looped line portions 118 between the elongated line portions 116. The elongated line portions 116 are oriented side-by-side to one another extending along the height 110 of the tubular body 106. The looped line portions 118 are oriented side-by-side to one another in two opposing rows 120, 121 spaced apart by the elongated line portions 116 and extending about the circumference 108 of the tubular body 106 such that the looped line portions 118 in one of the rows 120 are in staggered relationship to the looped line portions 118 in the other of the rows 121.

Figure 9:
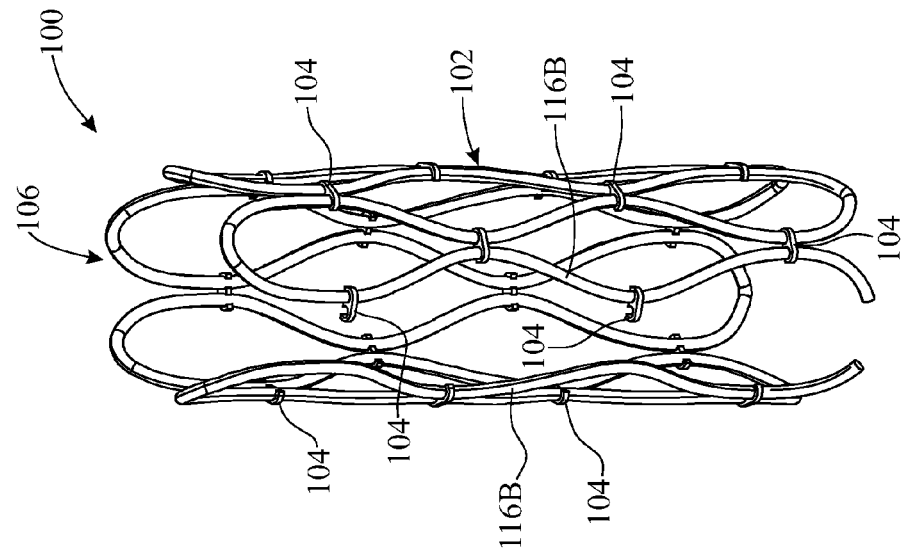
FIG. 9 presents a front isometric view of the partially assembled form of the garment rolled into a tubular body during the performance of the method of FIG. 6.

The connectors 104 respectively connect side-by-side pairs of the elongated line portions 116 of the elastic line 102 at multiple spaced locations thereon, for example four in number, along the height 110 of the tubular body 106 so as to orient each of the elongated line portions 116 in a sinuous (undulating, wavy or winding) pattern. The looped line portions 118, and the pairs of elongated line portions 116 connected by the connectors 104, provide the tubular body 106 in the form of an assembled tubular mesh netting structure having an endless sidewall and open opposite ends in which none of the elongated line portions 116 cross over one another, none of the looped line portions 118 cross over one another, and the connectors 104 are disposed about the exterior of the endless sidewall. (The assembled tubular mesh netting structure of the tubular body 106 forms the endless sidewall notwithstanding that the two opposite ends of the elastic line 102 do not connect with one another as can be seen in FIG. 9 in view that the elastic line 102 is not a continuous loop.)

Figure 4:
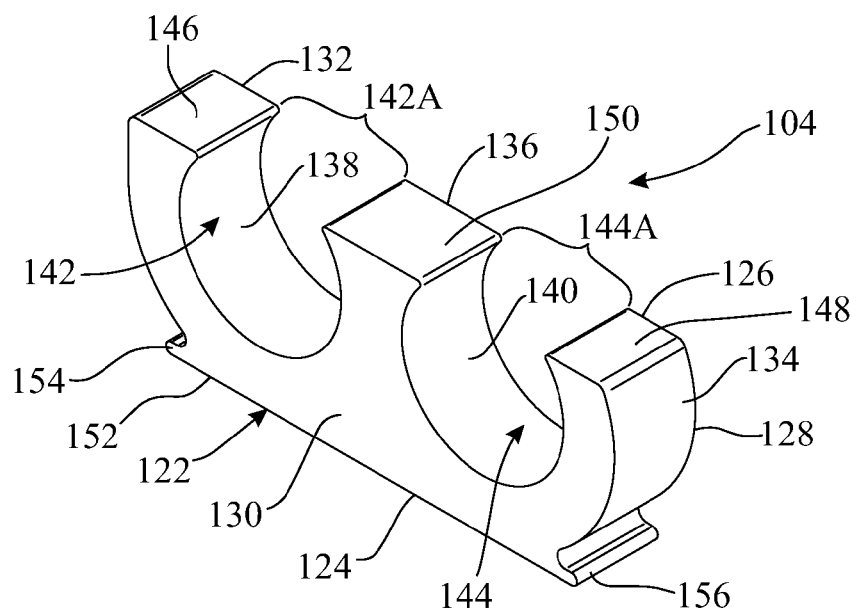
FIG. 4 presents an enlarged isometric view of an exemplary embodiment of a connector of a plurality thereof employed in the garment originally introduced in FIG. 1.

Each connector 104 is constructed to include a connector body 122 having top and bottom sides 124, 126, front and rear faces 128, 130, a pair of opposite outer end portions 132, 134, and an inner middle portion 136 disposed between and spaced from the opposite outer end portions 132, 134, as illustrated in FIG. 4. The outer end portions 132, 134 and inner middle portion 136 are also disposed between the top and bottom sides 124, 126 and front and rear faces 128, 130. Each of the outer end portions 132, 134 together with the inner middle portion 136 have mirror-imaged arch-shaped configurations defining a pair of arcuate surfaces 138, 140 substantially identical to one another in a spaced side-by-side relationship with one another within the connector body 122. Thus, the arcuate surfaces 138, 140 are disposed between the outer end portions 132, 134 and the inner middle portion 136, thereby being separated only by the inner middle portion 136 of the connector body 122. The pair of arcuate surfaces 138, 140, in turn, define a pair of passageways 142, 144 extending through the connector body 122 between the front and rear faces 128, 130 thereof. The passageways 142, 144 are spaced from the top side 124 of the connector body 122 and have respective openings 142A, 144A at the bottom side 126 of the connector body 122 through which each of a pair of the elongated line portions 116 of the elastic line 102 is received and removably retained in the passageways 142, 144. Each of the arcuate surfaces 138, 140, in defining one of the passageways 142, 144, circumscribes a portion of cylinder within a range of from about 220° to 250° and thereby with a diameter greater than the breadth of each of the openings 142A, 144A for engaging and retaining each of the pair of elongated line portions 116 of the elastic line 102 therein. The connector body 122 at the bottom side 126 thereof defines substantially flat co-planar surfaces 146, 148, 150 on the respective outer end portions 132, 134 and the inner middle portion 136, the surfaces 146, 148, 150 thereby being spaced from one another by the openings 142A, 144A of the passageways 142, 144. The connector body 122 at the top side 124 thereof defines a substantially flat surface 152 and a pair of oppositely protruding lips 154, 156 formed thereon at the opposite ends of the flat surface 152 on the top side 124. The lips 154, 156 are provided for gripping the connector 104 to assist in engaging the connector 104 upon and removing it from the pair of elongated line portions 116 of the elastic line 102. Alternatively, the surfaces 146, 148, 150, 152 may be more rounded than flat so as to avoid providing sharp edges on the connector 104. Also, the connector 104 may be made of any suitable material, such as by way of example but not of limitation a suitable plastic, and manufactured using any conventional technique such as molding.

Figure 5:
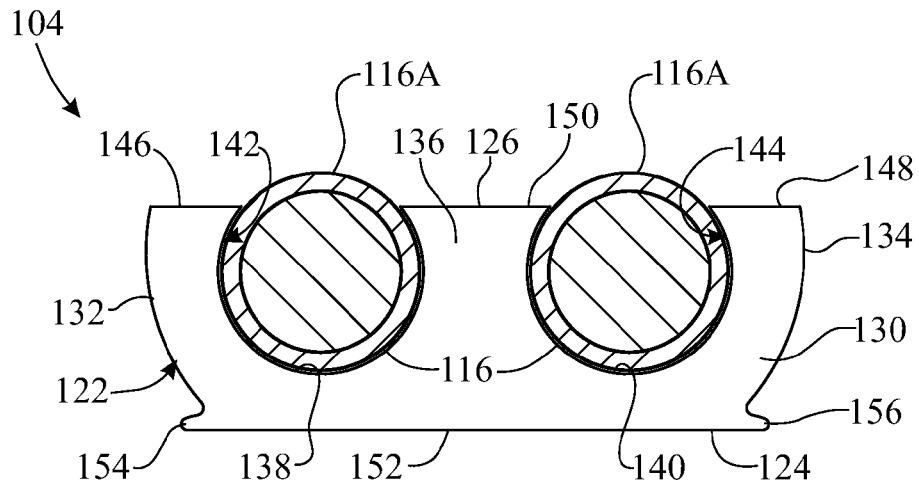
FIG. 5 presents an enlarged sectional view of a fragmentary portion of the garment originally introduced in FIG. 1, showing side-by-side portions of the line of elastic material connected by the connector of FIG. 4.

One side-by-side pair of the elongated line portions 116 of the elastic line 102 at corresponding locations thereof are shown tightly captured within the respective passageways 142, 144 of, and thereby connected by, the connector 104, as illustrated in FIG. 5. When each of the connectors 104 is in its connecting relationship with the one side-by-side pair of the elongated line portions 116 of the elastic line 102, small portions 116A of the elastic line 102 still protrude through the openings 142A, 144A of the passageways 142, 144 away from the connector 104 a sufficient distance to make contact with a surface of a wearer and at the same time to space the surfaces 140, 142, 144 on the bottom side of the connector 104 away from the skin surface of the wearer or the surface of an article of clothing on the wearer over which the garment 100 is worn.

Figure 6:
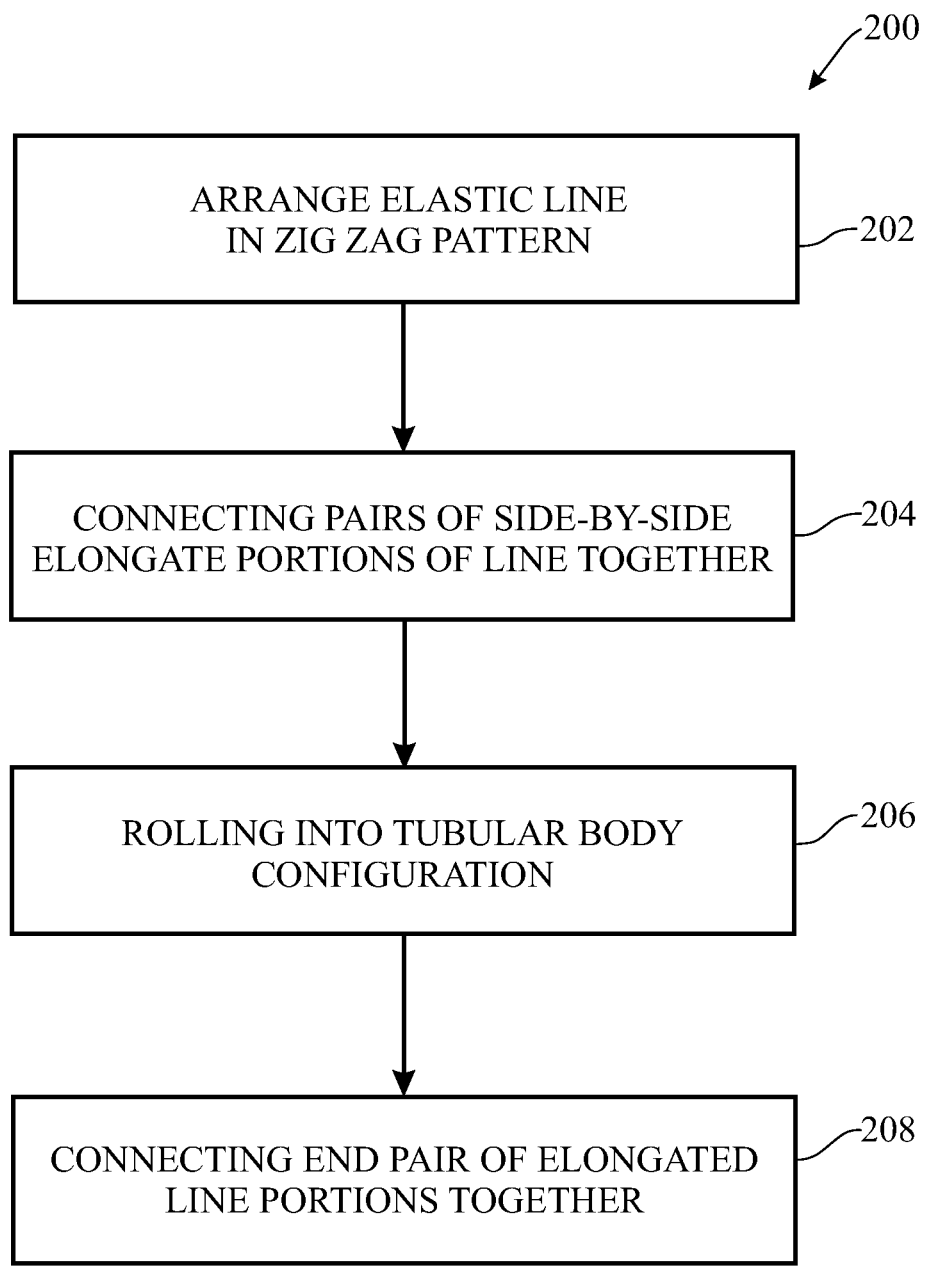
FIG. 6 presents a flow diagram illustrating an exemplary embodiment of a method of forming the garment originally introduced in FIG. 1.
Figure 7:
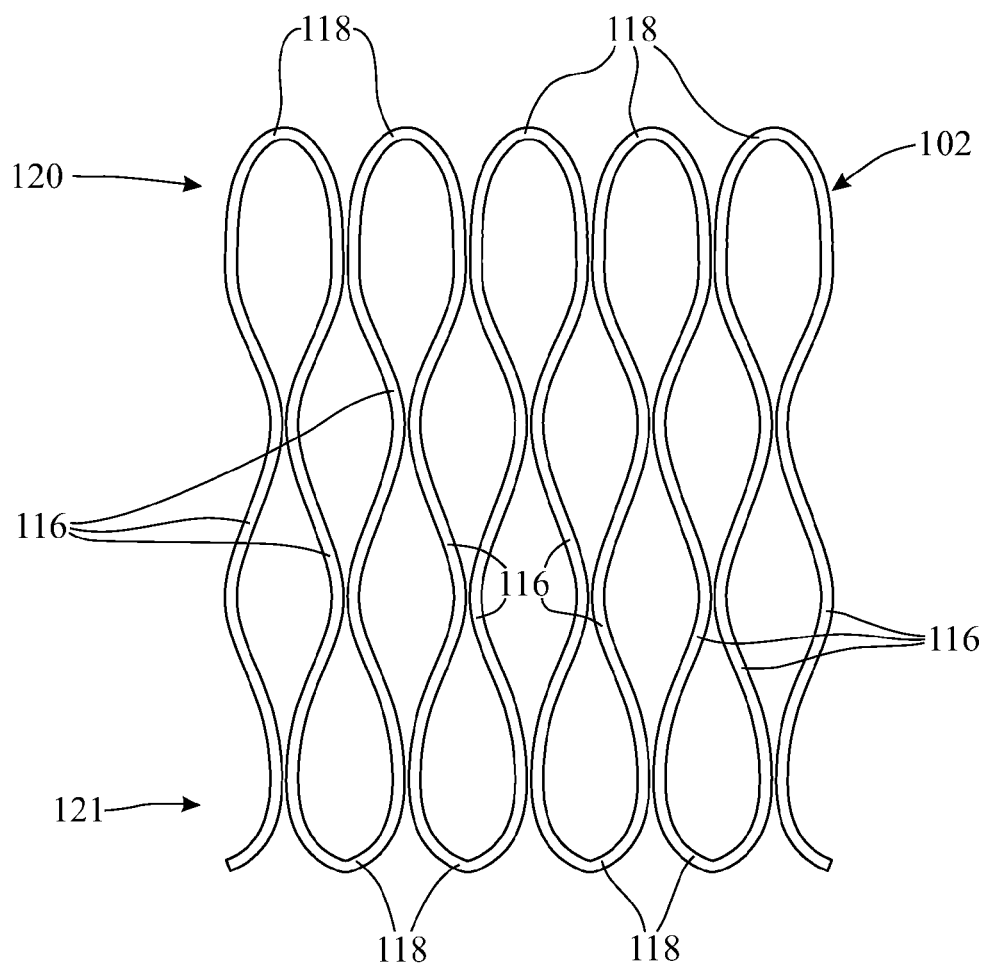
FIG. 7 presents a front elevation view of the line of elastic material of FIG. 2, laid out in a substantially zigzag pattern during performance of the method of FIG. 6.
Figure 8:
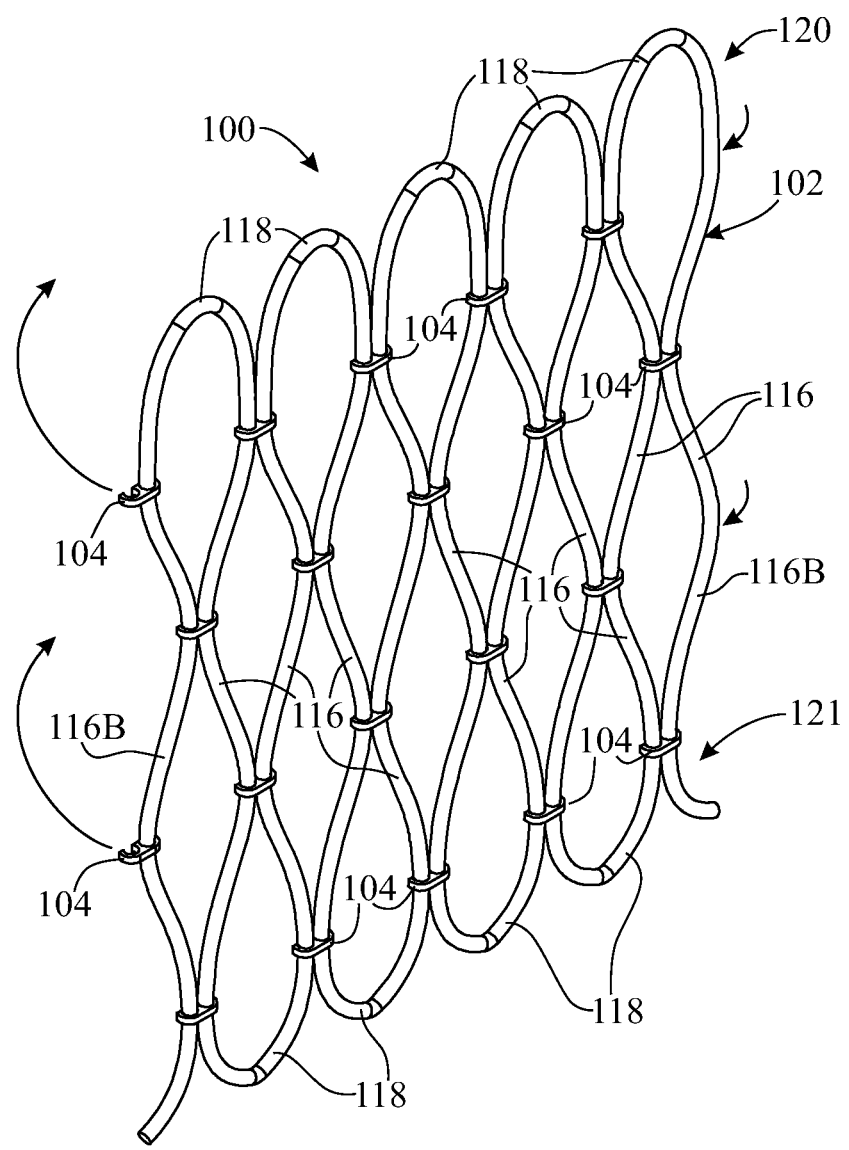
FIG. 8 presents a front isometric view of the garment in a partially assembled form during performance of the method of FIG. 6.

Referring to FIG. 6, there is illustrated a flow diagram 200 which shows the steps of an exemplary embodiment of a method of forming the garment 100. As per block 202 of the diagram 200, the elastic line 102 of FIG. 2 is arranged into a substantially zigzag pattern, as shown in FIG. 7, in which the elongated line portions 116 are oriented side-by-side to one another and the looped line portions 118 are oriented side-by-side to one another in two opposing rows 120, 121, being spaced apart by the elongated line portions 116. As can be readily observed in FIG. 7, the looped line portions 118 in one of the rows 120 are in a staggered relationship to the looped line portions 118 in the other of the rows 121. As per block 204 of the diagram 200, either contemporaneously with or following after the arrangement of the elastic line 102 in the zigzag pattern of FIG. 7, by using the connectors 104 the side-by-side elongated line portions 116 are connected to one another in pairs at the multiple spaced locations thereon so as to orient each of the elongated line portions 116 into a sinuous pattern. The looped line portions 118, together with the pairs of elongated line portions 116 connected by the connectors 104, provide a partially assembled mesh netting structure, as shown in FIG. 8, in which none of the elongated line portions 116 cross over one another and none of the looped line portions 118 cross over one another. As per block 206 of the diagram 200, either contemporaneously with or following after the connection of the side-by-side line portions 116 in pairs thereof as shown in FIG. 8, the partially assembled mesh netting structure of FIG. 8 is rolled into the configuration of the tubular body 106 shown in FIG. 9 wherein the elongated line portions 116 lie along the height 110 of the tubular body 106, the rows 120, 121 of the looped line portions 118 lie about the circumference 108 of the tubular body 106, and each of an opposite end pair of elongated line portions 116B of the tubular body 106 remain unconnected to one another. As per block 208 of the diagram 200, lastly, the unconnected opposite end pair of elongated line portions 116A are connected together by the connectors 104 at the multiple locations spaced thereon to provide the tubular body 106 in the form of the assembled tubular mesh netting structure of FIG. 1, having an endless sidewall and open opposite ends in which none of the elongated line portions cross over one another, none of the looped line portions cross over one another and the connectors 104 are disposed about the exterior of the endless sidewall.

Figure 10:
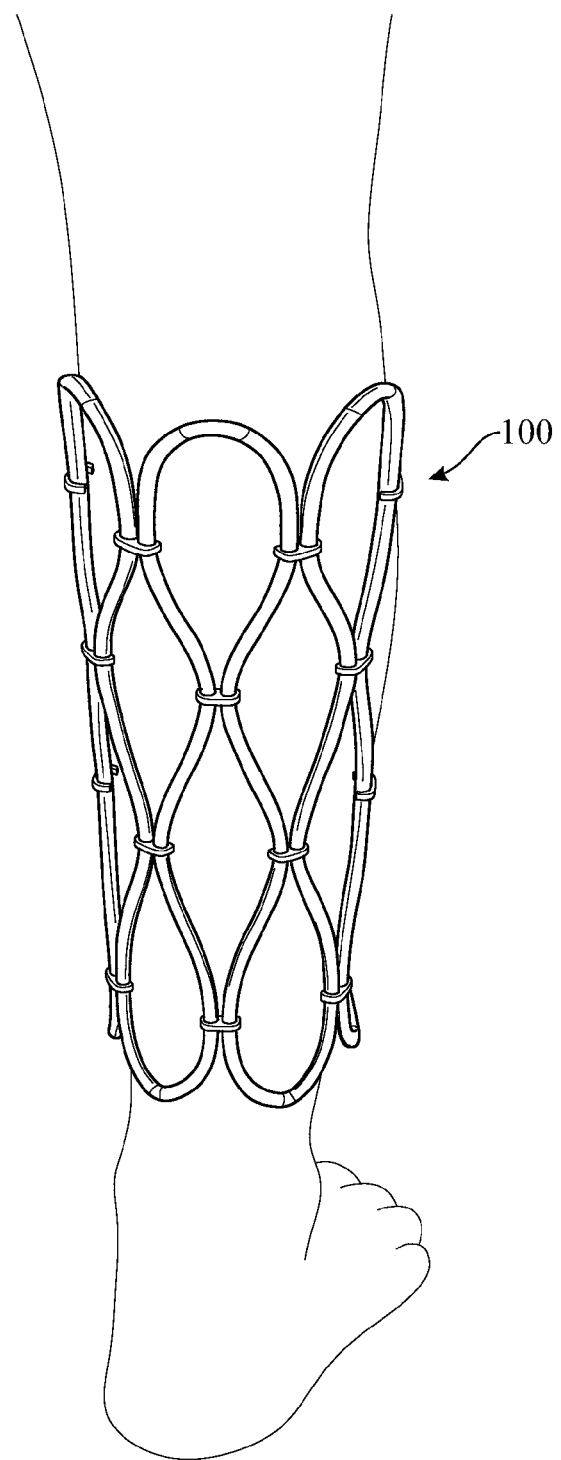
FIG. 10 presents a front isometric view of the garment originally introduced in FIG. 1, illustrating the garment being worn on a leg of a user.
Figure 11:
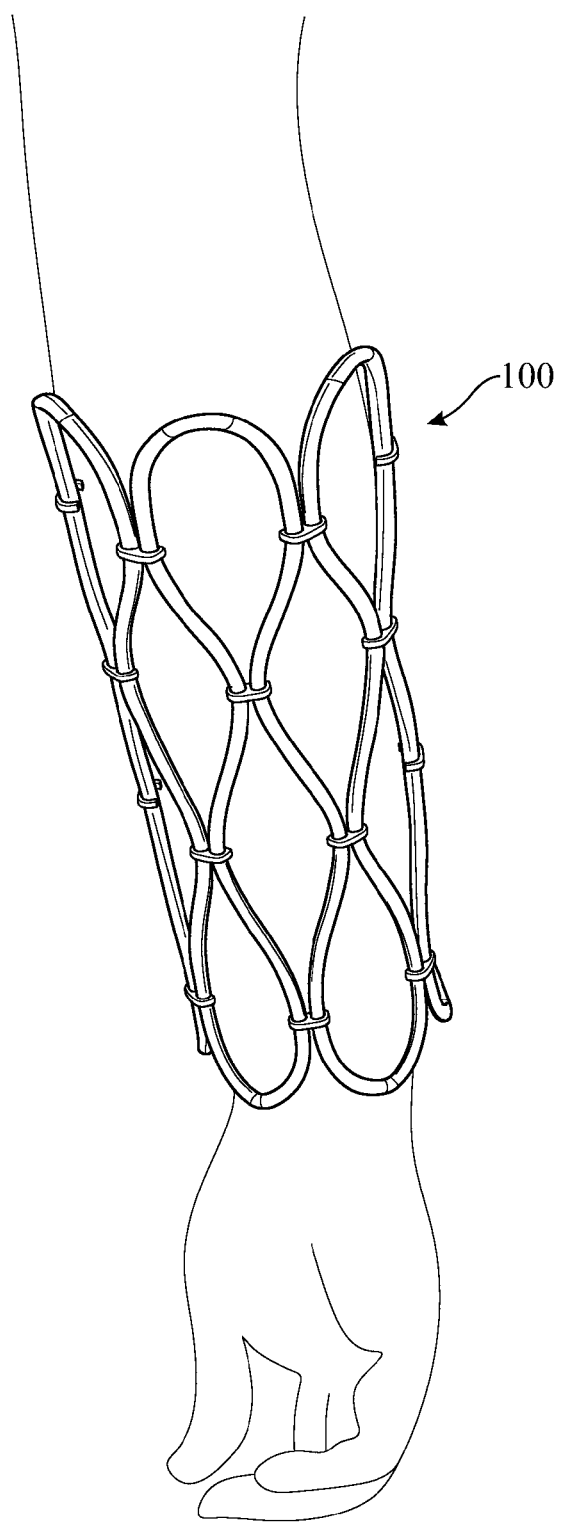
FIG. 11 presents a front isometric view of the garment originally introduced in FIG. 1, illustrating the garment being worn on an arm of a user.
Figure 12:
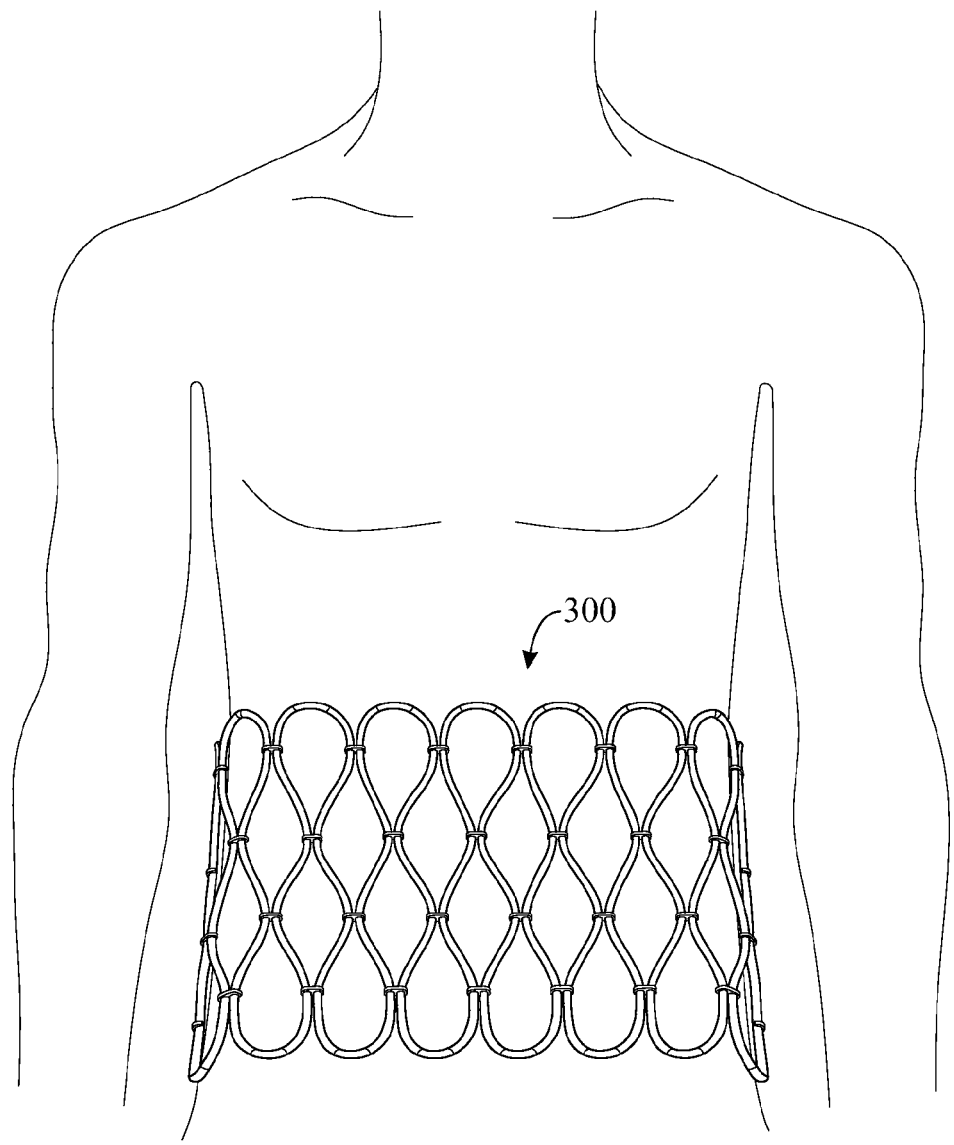
FIG. 12 presents a front isometric view of an alternative exemplary embodiment of a resistance-applying garment, illustrating the garment being worn on a torso of a user.

Referring to FIGS. 10-13, the garment 100 in FIGS. 10 and 11 is respectively shown worn on, or about, a leg of a wearer and on, or about, an arm of a wearer. Depending upon the comparative circumference sizes of the lower leg and the forearm of the wearer, the garment 100 may utilize an elastic line 102 having the same or different lengths depending on which application it is to be used for. Alternatively, a garment 300 can be worn on, or about, a torso of the wearer, as illustrated in FIG. 12. It is readily apparent that the torso is greater in circumference size compared to either the lower leg or forearm; thus, the garment 300 utilizes an elastic line 102 of greater length, or utilizes several elastic lines 102 forming several partially assembled mesh netting structures as shown in FIG. 8, to form the garment 400 in the manner shown in FIG. 13.

Figure 14:
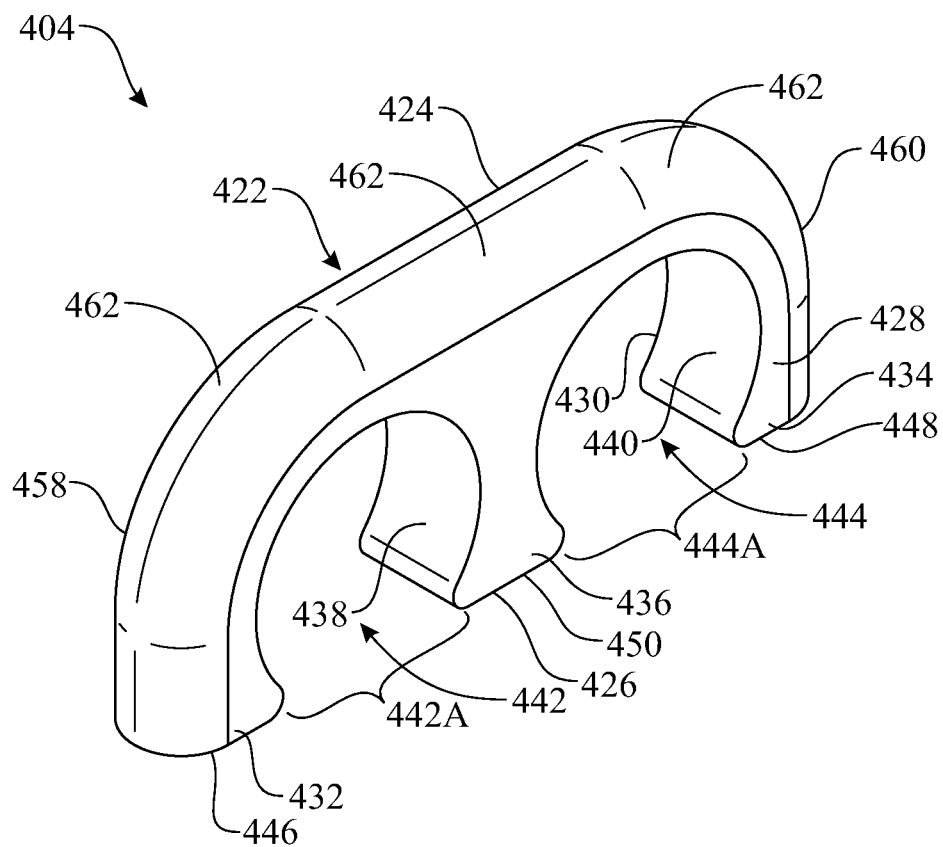
FIG. 14 presents an isometric view of an alternative embodiment of a connector of a plurality thereof that may be employed in the garment originally introduced in FIG. 1.

Referring now to FIG. 14, another exemplary embodiment, an alternative to the connector 104, is presented as a connector 404. Features of the connector 404, being the same as those of the connector 104, are numbered the same except preceded by the numeral '4'. The connector 404 includes a connector body 422 having top and bottom sides 424, 426, opposite outer sides 458, 460, front and rear faces 428, 430, a pair of opposite outer end portions 432, 434, and an inner middle portion 436 disposed between and spaced from the opposite outer end portion 432, 434. The outer end portions 432, 434 and inner middle portion 436 are also disposed between the top and bottom sides 424, 426, opposite outer sides 458, 460, and front and rear faces 428, 430. Each of the outer end portions 432, 434 together with the inner middle portion 436 have mirror-imaged arch-shaped configurations defining a pair of arcuate surfaces 438, 440 substantially identical to one another in a spaced side-by-side relationship with one another within the connector body 422. Thus, the arcuate surfaces 438, 440 are disposed between the outer end portions 432, 434 and the inner middle portion 436, thereby being separated only by the inner middle portion 436 of the connector body 422. The pair of arcuate surfaces 438, 440, in turn, define a pair of passageways 442, 444 extending through the connector body 422 between the front and rear faces 428, 430 thereof. The passageways 442, 444 are spaced from the top side 424 and the opposite outer sides 458, 460 of the connector body 422 and have respective openings 442A, 444A at the bottom side 426 of the connector body 422 through which each of a pair of the elongated line portions 116 of the elastic line 102 (not shown) is received and removably retained in the passageways 442, 444, the same as shown in FIG. 5 with respect to the connector 104. Each of the arcuate surfaces 438, 440, in defining one of the passageways 442, 444, circumscribes a portion of cylinder within a range of from about 220° to 250° and thereby with a diameter greater than the breadth of each of the openings 442A, 444A for engaging and retaining each of the pair of elongated line portions 116 of the elastic line 102 therein. The connector body 422 at the bottom side 426 thereof defines substantially flat co-planar surfaces 446, 448, 450 on the respective outer end portions 432, 434 and the inner middle portion 436, the surfaces 446, 448, 450 thereby being spaced from one another by the openings 442A, 444A of the passageways 442, 444. The connector body 422 at the top side 424 and the opposite outer sides 458, 460 thereof defines a substantially U-shaped outer surface 462 extending to the surfaces 446, 448 of the bottom side 426 and front and rear faces 428, 430 of the connector body 422. Instead of the oppositely protruding lips 154, 156 formed at the opposite ends of the flat surface 152 on the top side 124 of the connector body 122 of the exemplary embodiment of the connector 104 shown in FIGS. 4 and 5, the connector body 422 has the U-shaped outer surface 462 of the top side 424 and the opposite outer sides 458, 460 as seen in the alternative embodiment of FIG. 14. The U-shaped outer surface 462 is rounded or arcuate-shaped and extends to and between the front and rear faces 428, 430 of the connector body 422. This rounded configuration of the U-shaped outer surface 462 improves the wearability and function of the garment. The connector body 422 may be gripped at the portions of the front and rear faces 428, 430 along the middle portion 436 of the connector body 422 for gripping the connector 404 to assist in engaging the connector 404 upon and removing it from the pair of elongated line portions 116 of the elastic line 102. Also, the connector 404 may be made of any suitable material, such as by way of example but not of limitation a suitable plastic, and manufactured using any conventional technique such as molding.

In summary, as mentioned earlier, the garment 100 actually permits tailoring simultaneously in three ways to improve athletic performance during training: weight, air resistance and elastic resistance. First, the garment 100 provides the desired additional weight, uniformly distributed, over the body part, which will increase proximal muscle demand and therefore more resistance to those proximal muscles. Second, during fast moving athletic activities like running or biking, the garment 100 adds wind resistance or drag on the extremity in any plane of motion. Third, the garment 100 provides elastic resistance to muscles of the body part in all directions of movement, which resists muscle thickening during contraction while not interfering with performance of any sport. Finally, the garment 100 embraces the concept of exercise specificity, in that the closer the workout, while using the garment properly applied to the particular body part, represents the particular athletic activity the better the results attained.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. A resistance-applying garment, comprising:
    a line of elastic material arranged in a zigzag pattern; and
    a plurality of connectors connecting side-by-side pairs of portions of said line of elastic material so as to form an assembled tubular mesh netting structure having an endless sidewall and open opposite ends in which none of said portions of said line of elastic material cross over one another and said connectors are disposed about the exterior of said endless sidewall;
    wherein each of said connectors comprises
        a connector body having opposite top and bottom sides, opposite outer sides, front and rear faces, a pair of opposite outer end portions, and an inner middle portion disposed between and spaced from said outer end portions, said inner middle portion and said outer end portions also disposed between said top and bottom sides, said opposite outer sides, and said front and rear faces, and
        a pair of arcuate surfaces defined between said opposite outer end portions and said inner middle portion, said pair of arcuate surfaces defining a pair of passageways extending through said connector body between said front and rear faces thereof and spaced from said top side and said opposite outer sides and having respective openings at said bottom side of said connector body through which portions of said elastic line are received and removably retained in said passageways,
    wherein said top side and said opposite outer sides of said connector body define a U-shaped outer surface being arcuate-shaped and extending to and between said front and rear faces.

2. The garment of claim 1 wherein said line of elastic material ranges in thickness from about 6 mm to 14 mm.

3. The garment of claim 1 wherein said line of elastic material is one of an elastic string, cord, rope, cable or band.

4. The garment of claim 1 wherein said line of elastic material is a bungee cord.

5. A resistance-applying garment, comprising:
    a tubular body having a circumference and a height extending in a transverse relationship to the circumference, said tubular body being formed by:
        at least one line of elastic material arranged in a zigzag pattern so as to define a succession of elongated line portions and a succession of looped line portions between said elongated line portions such that said elongated line portions are oriented side-by-side to one another extending along the height of said tubular body and said looped line portions are oriented side-by-side to one another in two opposing rows spaced apart by said elongated line portions and extending about the circumference of said tubular body such that said looped line portions in one of said rows are in staggered relationship to said looped line portions in the other of said rows; and
        a plurality of connectors connecting side-by-side pairs of said elongated line portions at multiple spaced locations thereon along the height of said tubular body so as to orient each of said elongated line portions in a sinuous pattern such that said looped line portions, and said pairs of elongated line portions connected by said connectors, provide said tubular body in the form of an assembled tubular mesh netting structure having an endless sidewall and open opposite ends in which none of said elongated line portions cross over one another, none of said looped line portions cross over one another, and said connectors are disposed about the exterior of said endless sidewall;
    wherein each of said connectors comprises
        a connector body having opposite top and bottom sides, opposite outer sides, front and rear faces, a pair of opposite outer end portions, and an inner middle portion disposed between and spaced from said outer end portions, said inner middle portion and said outer end portions also disposed between said top and bottom sides, said opposite outer sides, and said front and rear faces, and
        a pair of arcuate surfaces defined between said opposite outer end portions and said inner middle portion, said pair of arcuate surfaces defining a pair of passageways extending through said connector body between said front and rear faces thereof and spaced from said top side and said opposite outer sides and having respective openings at said bottom side of said connector body through which each of a pair of said elongated line portions of said elastic line is received and removably retained in said passageways,
    wherein said top side and said opposite outer sides of said connector body define a U-shaped outer surface being arcuate-shaped and extending to and between said front and rear faces.

6. The garment of claim 5 wherein said line of elastic material ranges in thickness from about 6 mm to 14 mm.

7. The garment of claim 5 wherein said line of elastic material is one of an elastic string, cord, rope, cable or band.

8. The garment of claim 5 wherein said line of elastic material is a bungee cord.

9. The garment of claim 5 wherein said outer end portions together with said inner middle portion of said connector body have mirror-imaged arch-shaped configurations defining said pair of substantially identical arcuate surfaces within said connector body in a side-by-side relationship with one another being separated only by said inner middle portion of said connector body.

10. The garment of claim 5 wherein each of said arcuate surfaces circumscribes a portion of a cylinder within a range of from about 220° to 250° and thereby with a diameter greater than the breadth of said opening to each of said passageways for snugly engaging and retaining a pair of said elongated portions of said elastic line therein.

11. The garment of claim 5 wherein said connector body at said bottom side thereof defines substantially flat coplanar surfaces on said respective opposite outer end portions and said inner middle portion, said surfaces being spaced from one another by said openings of said passageways.

* * * * *